United States Patent [19]

van Gilse et al.

[11] 4,341,548
[45] Jul. 27, 1982

[54] N-(2-CYCLOHEXYLPHENYL)-N',N'-DIETHYL-ETHYLENE DIAMINE, ALGICIDAL COMPOSITIONS CONTAINING SAME, AND METHOD OF USE

[75] Inventors: Jaap van Gilse; Gerard B. Paerels, both of Weesp, Netherlands

[73] Assignee: Duphar International Research B.V., Netherlands

[21] Appl. No.: 270,826

[22] Filed: Jun. 5, 1981

Related U.S. Application Data

[63] Continuation-in-part of Ser. No. 59,420, Jul. 20, 1979, Pat. No. 4,286,983.

[30] Foreign Application Priority Data

Jul. 26, 1978 [NL] Netherlands ............... 7807908

[51] Int. Cl.$^3$ ............... A01N 33/06; C07C 87/62
[52] U.S. Cl. ............................. 71/67; 564/307
[58] Field of Search ............... 71/67; 564/307, 369

[56] References Cited

U.S. PATENT DOCUMENTS 3,871,862  3/1975  Merianos et al. ............ 71/67
4,286,983  9/1981  van Gilse et al. ............ 71/67

Primary Examiner—Paul M. Coughlan, Jr.
Attorney, Agent, or Firm—Stevens, Davis, Miller & Mosher

[57] ABSTRACT

There is disclosed N-(2-cyclohexylphenyl)-N', N'-diethyl-ethylene diamine. The compound is useful as an algicide. Compositions containing the compound and methods of use of the compositions are disclosed also.

5 Claims, No Drawings

N-(2-CYCLOHEXYLPHENYL)-N',N'-DIETHYL-ETHYLENE DIAMINE, ALGICIDAL COMPOSITIONS CONTAINING SAME, AND METHOD OF USE

REFERENCE TO RELATED APPLICATIONS

This application is a continuation-in-part of copending application Ser. No. 059,420 filed July 20, 1979, U.S. Pat. No. 4,286,983.

BACKGROUND OF THE INVENTION

The invention relates to a novel compound, an algicidal composition containing the novel compound, and to the prevention or control of algae with said composition.

Undesired growth of algae is an ever increasing phenomenon in surface waters, such as irrigation canals and drainage canals, fish ponds, wet rice fields, and the like. The quality or the flow of the water can be influenced very detrimentally by algae growth, as well as, as in the last example, the growth of the crop. Algae can also adhere to walls which are in contact with water, for example, ship's skins and wooden campshots. As a result thereof, a more frequent maintenance of the walls becomes necessary; in addition the algae limit the speed of the ship. Consequently an agent to prevent or to control algae is of great importance.

When applied to surface water, such an agent, however, should satisfy very stringent environmental requirements because only the growth of algae in the water is to be controlled; the evolution of other organisms living in the water may not be detrimentally influenced. Hence, the choice of a suitable algicide is much more critical than, for example, that of a herbicide because in the concentration used toxicity with respect to other forms living in the water should be entirely absent.

Netherlands Patent Application No. 68 18056 relates to algicidal compositions containing a diamine, for example N-(2,4,5-trichlorophenyl)-ethylenediamine as an active compound. However, this compound proves to be so toxic with respect to various organisms living in the water that the substance is not to be considered for controlling algae in surface water.

It has now been surprisingly found that undesired growth of algae can effectively be controlled without damaging the environment by using a composition which, in addition to a solid or liquid carrier material, comprises a compound of the formula

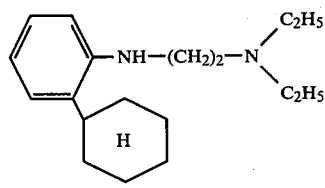

or a salt thereof.

The compound is also designated by the name N-(2-cyclohexylphenyl)-N',N'-diethyl-ethylene diamine.

As will become apparent from the examples, algae growth is prevented by the compositions according to the invention or the algae are efficiently killed. At the concentration at which a satisfactory algicidal activity is found, no toxicity is observed with respect to other living organisms in the water, such as fish.

The algicidal compositions according to the present invention are suitable for preventing or controlling all kinds of algae, such as Vaucheria, Cladophora, Mougeotia, Hydrodiction, Spirogyra, Eudogonium sp. and Enteromorpha. The dosage suitable for application will depend inter alia on the kind and population density of the algae to be controlled, and also on the conditions of the water, such as temperature, flow, pH and hardness, and on the soil conditions.

In the compositions of the invention, the active substance is mixed with solid carrier material or dissolved in liquid carrier material, possibly in combination with auxiliary substances, such as emulsifiers, dispersion agents, and stabilizers.

Examples of compositions according to the invention are aqueous solutions and dispersions, solutions in organic solvents, dispersible powders, pastes, miscible oils, granules, and pellets. Dispersible powders, pastes, and miscible oils are compositions in concentrate form which are diluted prior to or during use.

Some forms of compositions will be explained in detail hereinafter by way of example.

Granular compositions are prepared, for example, by taking up the active substance in a solvent or dispersing it in a diluent and impregnating the resulting solution or suspension, possibly in the presence of a binder, on a granular carrier material. A granular composition may also be manufactured by compressing the active substance in the presence of lubricants and binders, together with powdered minerals and disintegrating the compressed product to the desired grain size and sieving it.

Dispersible powders are prepared by mixing 10 to 80 parts by weight of a solid inert carrier with 10 to 80 parts by weight of the active substance, 1 to 5 parts by weight of a dispersing agent, for example, the lignin sulfonates or alkylnaphthalene sulfonates known for this purpose, and preferably also 0.5 to 5 parts by weight of a wetting agent, for example, fatty alcohol and sulfates, alkylarylsulfonates, fatty acid condensation products, or polyoxyethylene compounds.

For the preparation of miscible oils, the active compound is dissolved in a suitable solvent which is preferably poorly water-miscible and one or usually more emulsifiers is or are added to the solution. The concentration of the active compound in the miscible oils usually varies between 2 and 50 percent, by weight. In addition to a miscible oil may be mentioned as a liquid and highly concentrated primary composition, a solution of the active substance in a readily water-miscible liquid, to which solution a dispersing agent and possibly a surface-active substance has been added. Upon diluting with water shortly before or during spraying, an aqueous dispersion of the active substance is obtained.

For use in surface water, water-soluble or water-dispersible algicidal compositions are often used or granular compositions of pellets which cause the active substance to dissolve in the water at the desired rate. In order to improve the solubility or dispersibility in water, water-miscible solvents, such as acetone, glycol or glycol ethers may be used, as well as an emulsifier or a mixture of emulsifiers, for example, polyoxyethylene compounds.

For application to walls which are in contact with water ("antifouling"), the active substance is taken up in a wall-preservative, for example, a paint, a lacquer, or a tar.

Known algicidal and fungicidal compounds may also be incorporated in the compositions according to the invention. As a result thereof, the activity spectrum of the composition is widened and synergism may occur. To be considered for use in such a combination composition are known algicidal compounds, for example, urea compounds and triazines useful for this purpose and furthermore 7-oxabicyclo(2,2,1)heptane-2,3-dicarboxylic acid and 2-chloro-acetamido-3-chloro-1,4-naphthoquinone.

As suitable fungicides may be mentioned:
1. organic tin compounds, for example, triphenyl tin hydroxide and triphenyl tin acetate;
2. alkylenebisdithiocarbamates, for example, zinc ethylenebisdithiocarbamate and manganese ethylenebisdithiocarbamate;
3. 1-acyl- or 1-carbamoyl-N-benzimidazole (-2) carbamates and 1,2-bis(3-alkoxycarbonyl-2-thiureido)-benzene;
4. carboxanilides, for example, 5,6-dihydro-2-methyl-1,4-oxathiine-3-carboxanilides, methyl-substituted 5,6-dihydro-4H-pyrane-3-carboxanilide and methyl-substituted furane-3-carboxanilide and furthermore 2,4-dinitro-6-(2-octylphenyl)-crotonate, 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)tetrahydrophthalimide, N-dichlorofluoromethylthio-N-phenyl-N',N'-dimethylsulphamide, tetrachloroisophthalonitrile, 2-(4'thiazolyl)benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidine-methanol, 1-(isopropylcarbamoyl)-3-(3,5-dichlorophenyl)-hydantoine, N-(1,1,2,2-tetrachloroethylthio)-4cyclohexene-1,2-carboximide, N-trichloromethyl-mercapto-4-cyclohexene-1,2-dicarboximide, and N-tridecyl-2,6-dimethylmorpholine.

As already stated above, the dosage of the composition according to the invention desired for practical applications will depend on several factors. Generally, however, it holds that favorable results are achieved with a dosage which corresponds to 0.1 to 10 kg of the active substance per hectare of surface water, or 0.05 to 10 mg per liter of water. For application to walls which are in contact with water the active substance is taken up in a wall-preservative in a quantity of 0.2 to 10% by weight.

A few compounds which may be used in the algicidal compositions according to the invention are known from J. Am. Chem. Soc. 68, 2494 (1946) and J. Org. Chem. 26, 476 (1961). However, these publications do not state any pesticidal activity.

The new compound according to the invention can be prepared in a manner known per se for the synthesis of related compounds.

The invention will now be described in greater detail with reference to the following specific examples.

EXAMPLE 1

The algicidal activity of N-(2-cyclohexylphenyl)-N',N'-diethylethylenediamine was determined at the concentration set out in the table with the reported results (a comparative test with N-(4-cyclohexylphenyl)-N',N'-diethylethylenediamine was undertaken also and the results appear below).

The active substances were processed in compositions by dissolving or dispersing the compounds in water, if desired in the presence of a water-miscible solvent, namely ethoxyethanol, and a polyoxyethylenated ricinus oil as an emulsifier.

The water infested with algae was obtained by adding tap water to algae which were collected from a ditch. After the addition of the composition in various concentrations the algicidal activity was established by determining, 2 weeks after the addition, if, and if so to what extent, the algae were killed. The tests were performed on the following algae: Vaucheria, Cladophora, and Enteromorpha.

| Active Substance | conc. (mg/l) | algicidal activity (after two weeks) | | |
|---|---|---|---|---|
| | | Vaucheria | Cladophora | Enteromorpha |
| A | 1.0 | ++ | + | + |
| | 0.4 | ++ | + | ± |
| | 0.2 | ++ | ± | ± |
| | 0.1 | ++ | ± | ± |
| B | 1.0 | ++ | + | ++ |
| | 0.4 | ++ | + | + |
| | 0.2 | ++ | ± | + |
| | 0.1 | − | − | − |

A: N-(2-cyclohexylphenyl)-N',N'-diethyl-ethylenediamine
B: N-(4-cyclohexylphenyl)-N',N'-diethyl-ethylenediamine (for comparison purposes)
Table values:
− = no mortality at all
± = insufficient mortality
+ = moderate mortality
++ = substantially complete mortality

What is claimed is:
1. N-(2-cyclohexylphenyl)-N',N'-diethylethylenediamine and a salt thereof.
2. An algicidal composition comprising
   an algicidally effective amount of N-(2-cyclohexylphenyl)-N',N'-diethyl-ethylenediamine or a salt thereof and
   a solid or liquid inert material.
3. A method of preventing or controlling the growth of algae comprising treating the aqueous locus of said algae with an algicidally effective amount of the composition of claim 2.
4. The method of claim 3 wherein said algicidal composition is applied in a dosage corresponding to about 0.1 to about 10 kilograms of the active substance per hectare of surface water.
5. The method of claim 3 wherein said algicidal composition is applied in a dosage corresponding to about 0.05 to about 10 milligrams of the active substance per liter of water.

* * * * *